United States Patent [19]

Shimamura et al.

[11] 4,261,942
[45] Apr. 14, 1981

[54] PRODUCTION OF TABLETS OF SODIUM DICHLOROISOCYANURATE

[75] Inventors: Tadao Shimamura; Yasufumi Seo, both of Tokushima, Japan

[73] Assignee: Shikoku Kasei Kogyo Co., Ltd., Marugame, Japan

[21] Appl. No.: 88,587

[22] Filed: Oct. 26, 1979

[30] Foreign Application Priority Data

Oct. 30, 1978 [JP] Japan .................................. 53/134028

[51] Int. Cl.³ ............................................... B01J 2/00
[52] U.S. Cl. ...................................... 264/118; 264/141
[58] Field of Search ......................... 264/109, 118, 141

[56] References Cited

U.S. PATENT DOCUMENTS

| | | | |
|---|---|---|---|
| 3,886,249 | 5/1975 | Manganaro | 264/118 |
| 4,024,257 | 5/1977 | Kibbel, Jr. | 264/109 |
| 4,082,532 | 4/1978 | Imhof | 264/141 |

Primary Examiner—Donald E. Czaja
Assistant Examiner—James R. Hall
Attorney, Agent, or Firm—Thomas R. Morrison

[57] ABSTRACT

Tablets of sodium dichloroisocyanurate, produced with a specific moisture content, have flame resistance and thermal stability to avoid chain reaction thermal decomposition. Granular raw material for tabletting is prepared by forming columnar pellets of wet sodium dichloroisocyanurate obtained in the manufacturing process, drying the pellets to remove free water therein and to regulate the moisture content thereof to between 7 and 11%, compacting and crushing the pellets to obtain granules and then tabletting the granules under relatively low surface pressure.

10 Claims, 1 Drawing Figure

U.S. Patent     Apr. 14, 1981     4,261,942
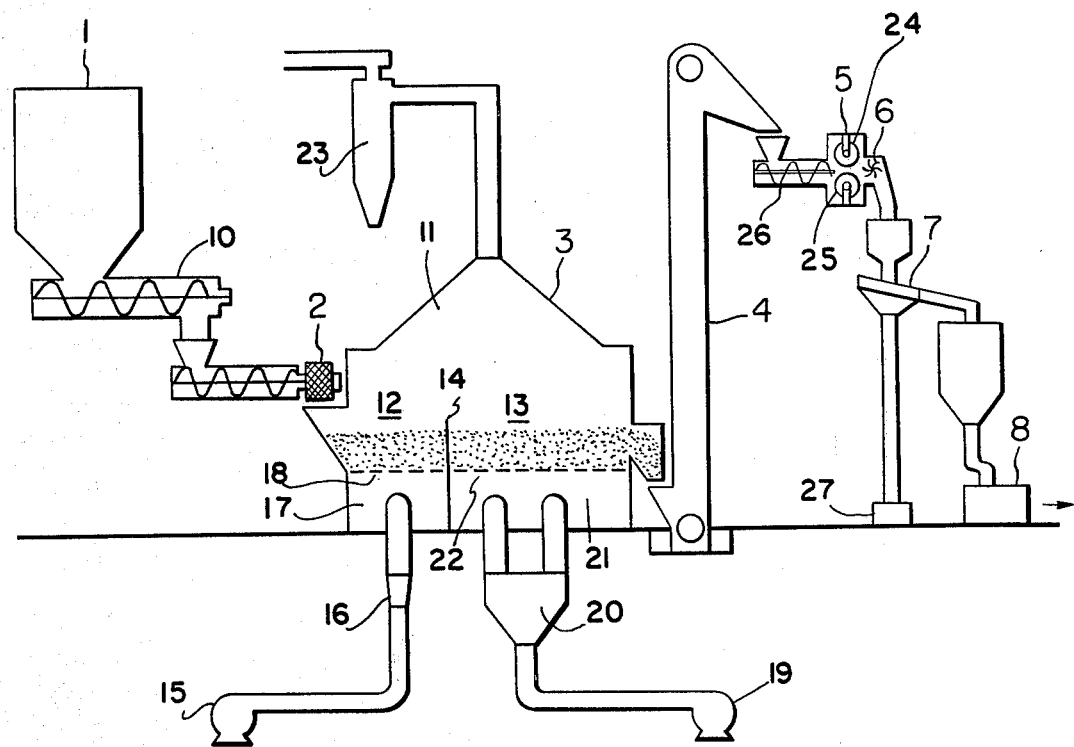

PRODUCTION OF TABLETS OF SODIUM DICHLOROISOCYANURATE

BACKGROUND OF THE INVENTION

1. Field of the Invention

The present invention relates to the production of tablets of sodium dichloroisocyanurate, and more particularly to the production of tablets having flame resistance and thermal stability sufficient to avoid chain reaction thermal decomposition.

Sodium dichloroisocyanurate is a widely used solid chlorine compound which is effective to release active chlorine for various purposes such as for sterilizing water in swimming pools and sewerage.

2. Description of the Prior Art

For storing, transportation and use, it is preferable to supply sodium dichloroisocyanurate in tablet form.

Production of sodium dichloroisocyanurate in tablet form is disclosed in Japanese Pat. No. 513,484 (Jap. Pat. Publn. No. 23 198/1967) granted to the assignee of the present patent application. In the referenced patent, sodium dichloroisocyanurate powder is kneaded with sufficient water to produce a predetermined water content in the resulting kneaded material. The kneaded material is compressed into tablets using a surface pressure of about 1,000 Kg/cm$^3$. U.S. Pat. No. 3,956,444 to William H. Kibbel, Jr. discloses sodium dichloroisocyanurate dihydrate tablets produced by a surface pressure of from about 2,000 to about 10,000 p.s.i.

The method disclosed in the Japanese patent has the disadvantage that wet dichloroisocyanurate is sticky. The stickiness adversely affects continuously supplying fixed amounts of the material to a tabletting machine. Therefore, this method is not suitable for use on an industrial scale.

The method of the United States patent has the advantage that tablets of sodium dichloroisocyanurate dihydrate produced thereby have flame resistance to avoid chain reaction thermal decomposition, but it has the disadvantage that, due to a water content of 14.1 weight %, it is sticky. The stickiness causes the same operational difficulty as in the Japanese patent. There is also the possibility that water may be released with a slight increase in heat in the tablet. Since the temperature at which the dihydrate is converted to the monohydrate lies at about 66.7° C., the resulting tablet products may be thus converted during storage and/or transportation and may cause agglomeration due to adhesion thereof.

SUMMARY OF THE INVENTION

Accordingly, a principal object of the present invention is to provide a method of producing tablets of sodium dichloroisocyanurate which can obviate and overcome the disadvantages involved in the prior art methods.

A specific object of the invention is to provide a method of producing tablets of sodium dichloroisocyanurate, which method can be easily and safely carried out on an industrial scale to make tablets having flame resistance, no thermal decomposition, and stability during storage and transportation without generating gas or caking.

Hitherto, it was known that sodium dichloroisocyanurate containing 11 weight % or more moisture has flame resistance and does not cause chain reaction decomposition. Anhydrous or hydrous sodium dichloroisocyanurate in the form of powder and granules containing 11 weight % or less moisture causes chain reaction combustion including a flame.

However, it has been discovered by the applicants that tablets obtained by tabletting sodium dichloroisocyanurate which was previously made into granules containing 7 to 11 weight % moisture have desirable flame resistance, do not cause thermal decomposition and have high stability during storage and transportation.

According to the present invention, therefore, the said and other objects are attained by producing tablets of sodium dichloroisocyanurate by tabletting granular sodium dichloroisocyanurate with moisture of 7 to 11 weight %.

It is preferable that the granules have a bulk density of 0.9 g/cm$^3$ or more. Such granules can be prepared by extruding wet sodium dichloroisocyanurate obtained in the manufacturing process through a screen with a large number of openings to form columnar pellets, passing the pellets through a fluidized bed heating chamber to dry the same until they contain substantially no free water and have a moisture content in the range of 7 to 11 weight %, compacting the dried pellets to bulk density of at least 0.8 g/cm$^3$, crushing the compacted pellets, then tabletting the granules under moderate pressure.

Moisture adjusted hot air can be fed to the fluidized heating chamber to obtain the pellets with a moisture content in the desired level. The monohydrate (having a moisture content of 7.6%) and the dihydrate (having a moisture content of 14.06%) have different vapor pressures at different temperatures. Thus, by adjusting the humidity and temperature of the hot air in the fluidized bed heating chamber, to balance the vapor pressure with that of the desired material emerging from the operation, either monohydrate or the dihydrate may be selectively obtained.

Furthermore, by appropriate temperature, humidity and residence time control, a mixture of monohydrate and dihydrate may be obtained.

The compacting and crushing steps may be carried out using a conventional roll type compactor and a conventional impeller type crusher, respectively. The resulting granules have a moisture content of 7 to 11 weight %, are not sticky and thus can be quite smoothly supplied to a tabletting machine in a fixed amount in each supply by simply charging the granules into a hopper of the tabletting machine without using an auxiliary feeding mechanism. The tabletting machine may be of any conventional type. The smooth supply of the granules in fixed amounts for each charging operation into the tabletting machine decreases the irregularity in amount for each tablet and helps bleed air from the gaps between neighboring granules during the tabletting operation. Such air gaps produce a so-called "capping phenomenon". Avoidance of such air gaps permits a hard tablet to be obtained at relatively low tabletting pressures. Further, the resulting tablets do not release free water to cause caking thereof, are easily handled and packaged, and they decrease the loss of active chlorine during storage. The tablets obtained by the method according to the present invention have a high effective chlorine content of 57 to 60%, compared to a chlorine content in sodium dichloroisocyanurate dihydrate of 55.4%.

BRIEF DESCRIPTION OF THE DRAWING

The single drawing shows a schematic illustration of an apparatus suitable for carrying out the method according to the present invention.

DETAILED DESCRIPTION OF THE PREFERRED EMBODIMENTS

Wet or moisture containing sodium dichloroisocyanurate for use in the present invention can be obtained using any suitable conventional manufacturing process. For instance, it can be produced by neutralizing dichloroisocyanuric acid with sodium hydroxide or reacting three components of trichloroisocyanurate, cyanuric acid and sodium hydroxide in a molar ratio of 2:1:3 in water, and then concentrating under reduced pressure or cooling the reaction mixture to separate and gather the resulting wet cake.

Referring now to the FIGURE, the wet raw material is contained in a raw material tank 1 having a screw feeder 10 and is extruded through a screen extruder type granulator 2 to form thin rods. Columnar pellets are formed from the rods by the breaking thereof from their own weight. The columnar pellets are dried in a fluidized bed type dryer 3. Fluidized bed type dryer 3 includes a drying chamber 11 which includes a first area 12 and a second area 13 separated by a divider 14. A blower 15 blows air through a moisture conditioning and heating element 16 into a region 17 below screen 18 of first area 12.

Similarly, a blower 19 provides air through a moisture conditioning and heating element 20 to a region 21 below a screen 22.

The columnar pellets breaking off from granulator 2 fall into first area 12 where they are supported by the air flowing thereinto through screen 18 and are dried as they move toward divider 14. The columnar pellets continue through second area 13 where they are further dried and/or moisture conditioned by air flowing through screen 22. During drying in dryer 3, the rods or pellets are broken into relatively short columnar pellets of substantially uniform size or length. At least the free water adhered to and contained in the pellets is removed and the total water content thereof is in the desired range.

Waste air from drying chamber 11 is exhausted through a cyclone-type separator 23 for removing dust and fine particles from the waste air.

The dried pellets pass from second area 13 into a vertical conveyor 4 which raises them to a screw-type conveyor 26 feeding a conventional roll type compactor 5 having a pair of rotary rolls 24 and 25. At least one of the rotary rolls 24 and 25 has a rough surface which is effective to compact the dried pellets with the aid of the other roll. The resulting compact pellets are crushed by a rotary impeller 6 to produce granules. The granules are fed to a vibrating screen 7 for dressing thereof and are then supplied to a tabletting machine 8 where the desired tablets are produced.

The diameter of each opening in the screen (not shown) of the screen extruder type granulator 2 is preferably from about 0.5 to about 3.0 mm and most preferably from about 1.5 to about 2.0 mm.

Moisture adjusted hot air containing about 26 g of water to 1 $Nm^3$ of dry air at a temperature of from about 50° to about 100° C. is supplied to the fluidized bed type dryer 3.

The water or moisture content of the wet sodium dichloroisocyanurate fed to the screen extruder type granulator 2 is regulated to a value of from about 15 to about 30%. A water content lower than 15% makes granulation difficult to accomplish. In addition, an observable powdering phenomenon appears during subsequent drying steps. A water content exceeding 30% permits the thin rod-like pellets formed by the granulator 2 to adhere to one another to form agglomerates in the drying step to make it impossible to uniformly dry them thus interfering with smooth and continuous operation.

The rotational frequency of the rolls 24 and 25 of the roll type compactor 5 is preferably set at a low level, such as, for example, 5 to 50 rpm. The pressure between the rolls of the roll type compactor 5 is preferably in a range of 500 to 1,500 Kg of force per linear centimeter of contact line between rolls 24 and 25.

The granules from the vibrating screen 7 have a size distribution in a range of 10 to 60 mesh, of which the main part lies in a range of 14 to 28 mesh. The average bulk density lies in a range of 0.8 to 1.2 $g/cm^3$. Excessively fine or coarse particles which pass vibrating screen 7 are recovered in a receiver 27.

Powdered or fine granules of sodium dichloroisocyanurate recovered from cyclone-type separator 23 and from receiver 27 may be recycling into raw material tank 1 by adding a predetermined amount of water or fresh raw material thereto to regulate the water content therein in preparation for again passing this material through the screen extruder type granulator 2.

Tabletting pressure in tabletting machine 8 is preferably at least 350 $Kg/cm^2$ and more preferably from about 350 to about 750 $Kg/cm^2$ to impart flame resistance to the product. Higher pressure values are not always necessary for the tabletting operation. If necessary, a small amount of a lubricant such as a metal salt of stearic acid may be mixed with the granules prior to supplying them to the tabletting machine.

The tablets obtained by the method according to the invention in which no lubricant is used have a bulk density of 1.3 to 1.5 $g/cm^3$, contain 7 to 11 weight % moisture and have good solubility in water.

The method according to the invention ensures safety during the operation. The chemically unstable wet sodium dichloroisocyanurate is first extruded through the screen extruder type granulator 2 under a low loading pressure. The resulting pellets are dried to a chemically stable state in which they contain substantially no free water. The dried pellets are compacted in roll type compactor 5 under high loading pressure. The resulting compacted granules are crushed in rotary impeller 6 and then are tabletted in tabletting machine 8 to obtain the final product.

EXAMPLE 1

Powdery solids of dichloroisocyanurate containing 25.0% moisture and stored in a raw material tank 1 were continuously fed by a screw feeder at a rate of 200 Kg/hr to a screen extruder type granulator 2 with a screen having a large number of openings, each of which had a diameter of 1.5 mm to extrude therefrom the raw material to form thin rods which broke off of their own weight to form columnar pellets which fell into first area 12 of drying chamber of a fluidized bed type dryer 3. Fluidized bed type dryer 3 had a surface area of 0.75 $m^2$ and air heated in a temperature range of from about 75° to about 85° C. and containing 25.9 g of moisture to 1 Nm³ of dry air was continuously supplied. The pellets passed through the dryer chamber over an average residence time of 20 minutes to form pellets of sodium dichloroisocyanurate hydrate containing 10.0% moisture.

The resulting pellets were compacted in a roll type compactor 5, crushed by a rotary impeller 6 and then sieved by a vibrating screen 7 to recover granules of 60 or below in mesh-size. The resulting granules had an average bulk density of 0.93 g/cm³.

The granules were fed to a tabletting machine 8 to continuously prepare tablets at a surface pressure of 500 Kg/cm². The tablets had an average weight of 15 g. The operation was continued for 12 hours and 1,300 Kg of produce was produced.

The tablets produced had an average bulk density of 1.45 g/cm³ and showed good flame resistance. The weight deviation of the product was ±2.0%.

As a comparative example, sodium dichloroisocyanurate powder containing 10.0% moisture was fed to the tabletting machine without performing the other steps of the process. The supply of raw material became unstable and the capping phenomenon occurred which required slowing the tabletting operation. The yield of product for 12 hours operation was limited to 940 Kg. The weight deviation of the product was ±5.0%.

EXAMPLE 2

Grooves 10 mm in depth, 20 mm in width and 100 mm in length were cut in porous fire-brick. One set of grooves was packed to a density of about 1.0 g/cm³ with granular sodium dichloroisocyanurate containing various amounts of moisture. Another set of grooves was packed to about 0.7 g/cm³ with powdered sodium dichloroisocyanurate containing various amounts of moisture. A hot nichrome wire was applied to one end of each filled groove to attempt to cause chain-reaction thermal decomposition. The time required for transmitting thermal decomposition a distance of 50 mm was measured for each case. The results are shown in Table 1.

TABLE 1

| Moisture content | Transmission velocity (sec) | |
|---|---|---|
| of samples | Granular form | Powder form |
| 1.6 | 83 | — |
| 2.8 | — | 233 |
| 5.0 | 123 | — |
| 7.0 | 255 | — |
| 9.5 | — | 325 |
| 10.0 | naturally extinguished after 25 mm | 350 |
| 10.5 | no transmission | 412 |
| 11.0 | " | naturally extinguished after 30 mm |
| 11.5 | " | no transmission |

The results show that chain-reaction thermal decomposition occurs when the moisture content is less than 10% and 11% for granular and powdered sodium dichloroisocyanurate, respectively.

EXAMPLE 3

Tablets of sodium dichloroisocyanurate were prepared in accordance with the method as described in Example 1 having different moisture contents and tabletting pressures. Each tablet was placed on a nichrome wire having a length of 200 mm and electric resistance of 0.8Ω arranged on porous fire-brick. The relation between the moisture content of each tablet and the transmission time of thermal decomposition thereof was measured. The results are shown in Table 2.

TABLE 2

| Moisture | Tabletting at surface pressure of | |
|---|---|---|
| content | 350 Kg/cm² | 750 Kg/cm² |
| 1.6 | Completely decomposed in 120 sec. | Completely decomposed in 134 sec. |
| 5.0 | Completely decomposed in 178 sec. | Completely decomposed in 210 sec. |
| 7.0 | Naturally extinguished after some transmission | Naturally extinguished after some transmission |
| 7.6 | No decomposition | No decomposition |
| 10.0 | " | " |
| 11.0 | " | " |
| 13.5 | " | " |

The results show that the thermal stability of sodium dichloroisocyanurate in tablet form is far better than that in the form of granule or powder and that the sodium dichloroisocyanurate tablets containing moisture of more than 7.0 do not support chain-reaction thermal decomposition.

EXAMPLE 4

A number of sodium dichloroisocyanurate tablets containing different percentages of moisture were prepared in accordance with the method as described in Example 1 using tabletting surface pressure of 500 Kg/cm². The different moisture contents were produced by varying the residence time of the tablets in the fluidized bed type dryer 3. Twenty tablets of each kind, each tablet having a weight of 15 g, were sealed in glass bottles of 300 ml and stored in a constant temperature chamber maintained at 30° C. The amount of generated decomposed gas was measured by the change in height of a column of a saturated aqueous solution of sodium chloride which was communicated to the sealed bottle. Caking of the pellets was noted by visual observation. The results are shown in Table 3.

TABLE 3

| | Amount of decomposed gas (height of column in mm) | | |
|---|---|---|---|
| Moisture content | After 30 days | After 60 days | State of caking |
| 1.6 | 15 | 17 | none |
| 5.0 | 10 | 12 | " |
| 7.6 | 14 | 20 | " |
| 10.0 | 25 | 40 | " |
| 11.0 | 50 | 96 | slight |
| 13.5 | 896 | 1290 | apparent |
| 14.1 | 1770 | 3246 | " |

The results show that generation of decomposed gas becomes marked when the moisture content of the tablets exceeds 11% and especially when the moisture content of the tablets exceeds 14.1%. The tablets may release more or less free water accompanying vigorous generation of decomposed gas. An observable caking phenomenon appears when the moisture content of the tablets exceeds 11%.

EXAMPLE 5

Sodium dichloroisocyanurate tablets were prepared in accordance with the method as described in Example 1, having different moisture contents and tabletting surface pressure. The moisture content was controlled by varying the residence time of the tablets in the fluidized bed type dryer 3. Each kind of tablet was placed in a constant temperature chamber maintained at 30° C. and at a humidity of 72%. Dissolubility of the tablets was checked to obtain the results shown in Table 4.

The dissolubility was determined by placing each tablet having a weight of 15 g on a wire-netting with ½ inch stitches, submerging it in stirred water at 20° C., and measuring the time required for it to become completely dissolved in the water.

TABLE 4

| Moisture content (%) | Tabletting pressure (Kg/cm$^2$) | Time for dissolution (sec) | | |
|---|---|---|---|---|
| | | Just after tabletting | Stand for 24 hours after tabletted | Stand for 48 hours after tabletted |
| 6.0 | 350 | 185 | 300 | 420 |
| | 500 | 200 | 350 | 500 |
| | 750 | 260 | 480 | 530 |
| | 1000 | 300 | 520 | 550 |
| 10.0 | 350 | 330 | 290 | 350 |
| | 500 | 325 | 330 | 380 |
| | 750 | 320 | 330 | 390 |
| | 1000 | 320 | 350 | 420 |
| 13.0 | 350 | 35 | 250 | 380 |
| | 500 | 75 | 260 | 410 |
| | 750 | 135 | 340 | 430 |
| | 1000 | 420 | 310 | 530 |

The tablets containing more than 11% moisture were observed to shrink when stored in humid conditions. Tablets containing less than 10% moisture were observed to expand under the same humid conditions. Tablets containing 13 and 6% moisture have a high variation in dissolubility depending on the elapsed time after tabletting. Tablets containing 10% show substantially constant dissolubility over time.

Having described specific embodiments of the invention with respect to the accompanying drawings, it is to be understood that the invention is not limited to those precise embodiments, and that various changes and modifications may be effected therein by one skilled in the art without departing from the scope or spirit of the invention as defined in the appended claims.

I claim:

1. A method of producing sodium dichloroisocyanurate tablets comprising:

forming pellets of sodium dichloroisocyanurate containing from about 15 to about 30 weight % of water;

drying said pellets to remove substantially all free water therefrom and to reduce the moisture content thereof to the range from about 7 to about 11 weight %;

compacting the dried pellets to a bulk density of at least about 0.8 g/cm$^3$;

crushing the compacted dried pellets to obtain granular sodium dichloroisocyanurate; and tabletting the crushed compacted dried pellets using a tabletting pressure of at least 350 Kg/cm$^2$.

2. A method as claimed in claim 1, wherein said tablets have a bulk density of from about 1.3 to about 1.5 g/cm$^3$.

3. A method as claimed in claim 1, wherein said step of forming pellets includes extruding wet sodium dichloroisocyanurate through a screen with a number of openings to form thin rods which break of their own weight to form columnar pellets.

4. A method as claimed in claim 3, wherein each of said openings in said screen has a diameter of from about 0.5 to about 3.0 mm.

5. A method as claimed in claim 4, wherein each of said openings in said screen has a diameter of from about 1.5 to about 2.0 mm.

6. A method as claimed in claim 3, which includes performing said drying step in a fluidized bed type dryer and supplying air containing about 26 g moisture to 1 Nm$^3$ dry air heated to a temperature ranging from about 50° to about 100° C. to said fluidized bed type dryer.

7. A method as claimed in claim 1, wherein said compacting is carried out by a roll type compactor having a pair of rolls which rotate at from about 5 to about 50 rpm and impart a load of from about 500 to about 1,500 Kg per linear cm of contact line.

8. A method as claimed in claim 1, wherein the bulk density of said dried pellets after compacting lies in a range of from about 0.8 to about 1.2 g/cm$^3$.

9. A method as claimed in claim 1, wherein said crushing is performed by a rotary impeller.

10. A method as claimed in claim 1 wherein said tabletting pressure is from about 350 to about 750 Kg/cm$^2$.

* * * * *